(12) United States Patent
Park et al.

(10) Patent No.: US 7,053,372 B2
(45) Date of Patent: May 30, 2006

(54) STANDARD SAMPLE FOR TRANSMISSION ELECTRON MICROSCOPE (TEM) ELEMENTAL MAPPING AND TEM ELEMETAL MAPPING METHOD USING THE SAME

(75) Inventors: Gyeong-su Park, Gyeonggi-do (KR); Kazutoshi Kaji, Hitachi (JP); Jong-bong Park, Gyeonggi-do (KR); Shohei Terada, Hitachi (JP); Tatsumi Hirano, Hitachi (JP); Se-ahn Song, Seoul (KR)

(73) Assignees: Samsung Electronics Co., Ltd., Suwon-si (KR); Hitachi, Ltd., Tokyo (JP); Hitachi High-Technologies Co., Tokyo (JP)

( * ) Notice: Subject to any disclaimer, the term of this patent is extended or adjusted under 35 U.S.C. 154(b) by 0 days.

(21) Appl. No.: 11/034,721

(22) Filed: Jan. 14, 2005

(65) Prior Publication Data
US 2005/0184233 A1    Aug. 25, 2005

(30) Foreign Application Priority Data
Jan. 16, 2004   (KR) .................... 10-2004-0003253

(51) Int. Cl.
*G01N 23/02* (2006.01)
*H01J 37/26* (2006.01)

(52) U.S. Cl. .................... 250/311; 250/306; 250/307; 250/492.2; 250/492.3

(58) Field of Classification Search .................... None
See application file for complete search history.

(56) References Cited

U.S. PATENT DOCUMENTS 6,231,668 B1   5/2001  Loesch et al.
6,420,703 B1   7/2002  Wu et al.

*Primary Examiner*—Nikita Wells
(74) *Attorney, Agent, or Firm*—Buchanan Ingersoll PC

(57) ABSTRACT

A standard sample for transmission electron microscopy (TEM) elemental mapping and a TEM elemental mapping method using the same are provided. The standard sample includes a substrate; a first crystalline thin film containing heavy atoms formed on the substrate; a first amorphous thin film having oxides or nitrides containing light atoms and having a thickness of 1–5 nm or 6–10 nm formed on the first crystalline thin film; a second crystalline thin film containing heavy atoms formed on the first amorphous thin film. The standard sample can be used to correct TEM, EDS and EELS mapping results of a multi-layered nanometer-sized thin film and to optimize mapping conditions.

26 Claims, 6 Drawing Sheets

---

MEASURING THE ROUGHNESS AND THICKNESS ($T_1$) OF A STANDARD LAYER USING TEM & XRR

⇩

ELEMENTAL MAPPING BY EDS AND EELS TECHNIQUES AT VARIOUS CONDITIONS AND MEASURING THE THICKNESS ($T_2$) OF A STANDARD LAYER FROM THE MAPPING IMAGE

⇩

ELEMENTAL MAPPING OF SAMPLE THIN FILM BY EDS AND EELS OF TEM AT THE CONDITION WHEN $T_2-T_1$ IS MINIMUM

MEASURING THE ROUGHNESS AND THICKNESS ($T_1$) OF A STANDARD LAYER USING TEM & XRR

ELEMENTAL MAPPING BY EDS AND EELS TECHNIQUES AT VARIOUS CONDITIONS AND MEASURING THE THICKNESS ($T_2$) OF A STANDARD LAYER FROM THE MAPPING IMAGE

ELEMENTAL MAPPING OF SAMPLE THIN FILM BY EDS AND EELS OF TEM AT THE CONDITION WHEN $T_2 - T_1$ IS MINIMUM

STANDARD SAMPLE FOR TRANSMISSION ELECTRON MICROSCOPE (TEM) ELEMENTAL MAPPING AND TEM ELEMETAL MAPPING METHOD USING THE SAME

BACKGROUND OF THE INVENTION

Priority is claimed to Korean Patent Application No. 10-2004-0003253, filed on Jan. 16, 2004, in the Korean Intellectual Property Office, the disclosure of which is incorporated herein in its entirety by reference.

1. Field of the Invention

The present invention relates to a standard sample for transmission electron microscope (TEM) elemental mapping and TEM elemental mapping using the same, and more particularly, to a standard sample for transmission electron microscope (TEM) elemental mapping which can be used to correct results of elemental mapping of nanometer-sized thin films, which are obtained by energy dispersive spectroscopy (EDS) and electron energy loss spectroscopy (EELS) methods using TEM, and to optimize mapping conditions, and TEM elemental mapping method using the same.

2. Description of the Related Art

Recently, industrialized countries have strategically intensified ISO international standardization activities to widen the world's industrial market. In particular, public research centers where analyzing equipment is operated, government-sponsored research centers, corporate research centers, analyzing service centers, and the like have contributed to the formation of a large-scale analysis marketplace. In this market, a microbeam analysis technique plays a pivotal role in R&D and industrialization of nanometer scale techniques. However, the microbeam analysis technique has not been standardized, and also the manufacture, research, and development of standard samples for microbeam analysis are far behind a desirable level.

An elemental mapping method is an imaging technique in which 2-dimentional images of the layer structure and the elemental distribution of multi-layered thin films are produced. Transmission electron microscope (TEM) mapping methods, which are used to obtain elemental mapping images of multi-layered thin films, can be divided into energy dispersive spectroscopy (EDS) mapping using a characteristic X ray and electron energy loss spectroscopy (EELS) mapping. Since thicknesses of multi-layered thin films included in devices are on a micro-scale, the resolution of an elemental mapping device must be on a nanometer scale. Accordingly, a standard sample is needed to correct elemental mapping images and to optimize mapping conditions.

In TEM elemental mapping of nanometer sized thin films, the thickness, chemical composition, and distribution of a standard sample must be precisely known. As a result, the standard sample must have a structure, which can be easily analyzed to obtain the thickness, elements, and the structure thereof.

In order to analyze a multi-layered thin film sample having a thickness of 1–2 nm, X-ray reflectivity (XRR) and TEM, rather than scanning electron microscopy (SEM) or ellipsometry, are preferred to efficiently obtain precise analysis results. If TEM is used to analyze the elements and the structure of a nanometer-sized thin film having the thickness of 1–2 nm, TEM/EDS using a field emission electron gun and TEM/EELS are used.

A conventional TEM elemental mapping method used on a nanometer-sized thin film includes identifying an element of which the nanometer-sized thin film is composed using EDS and EELS, selecting a peak energy corresponding to the element, and performing elemental mapping under a condition in which the signal to noise ratio (S/N) is good. Although a mapping image formed from the nanometer-sized thin film using this method has a nanometer-sized thin film thickness difference of about 1–5 nm depending on mapping methods and conditions, the mapping thickness difference has been ignored because it is relatively small.

In principle, the use of the EDS mapping method results in a decrease in spatial resolution power of a mapping image since a characteristic X ray, which is generated when an impinging beam diffuses in a sample, is used. In addition, the spatial resolution of a mapping image can be changed by altering an acceleration voltage, a probe size, sample drift, and a sample thickness. The EELS mapping method can be used to realize an elemental mapping image of nanometer-sized thin films by high spatial resolving power because a sub-nanometer scale probe size can be obtained by FE-TEM. However, a SNR varies according to a sample thickness and an element being mapped. Additionally, depending on EELS mapping conditions, energy drift, sample drift, a probe size, and delocalization have various influences on the spatial resolution of the mapping image. These variables result in a mapping thickness difference between a measured thickness and a real thickness.

U.S. Pat. No. 6,231,668 discloses an image correction specimen for a scanning electron microscope (SEM), a scanning transmission electron microscope (STEM), and a scanning probe microscope (SPM). The image correction sample is prepared by sequentially depositing crystalline or amorphous heterolayers with different compositions. The thickness of the individual layers are less than 25 nanometers. U.S. Pat. No. 6,420,703 discloses a SEM correction standard sample in which straight metal lines having a uniform line width of less than 20 nm and a length of several tens of µm are formed using a focused ion beam technique.

SUMMARY OF THE INVENTION

The present invention provides a standard sample for transmission electron microscopy (TEM) elemental mapping which can be used to correct results of elemental mapping of nanometer-sized thin films, which are obtained by EDS and EELS methods using TEM, and optimize a mapping condition, and a TEM elemental mapping method using the same.

According to an aspect of the present invention, there is provided a standard sample for transmission electron microscope elemental mapping, the standard sample including:

a substrate;

a first crystalline thin film containing heavy atoms formed on the substrate;

a first amorphous thin film comprising oxides or nitrides containing light atoms and having a thickness of 1–5 nm formed on the first crystalline thin film; and a second crystalline thin film containing heavy atoms formed on the first amorphous thin film.

According to another aspect of the present invention, there is provided a standard sample for transmission electron microscope elemental mapping, the standard sample including:

a substrate;

a first crystalline thin film containing heavy atoms formed on the substrate;

a first amorphous thin film comprising oxides or nitrides containing light atoms and having a thickness of 6–10 nm formed on the first crystalline thin film; and a second crystalline thin film containing heavy atoms formed on the first amorphous thin film.

According to still another aspect of the present invention, there is provided a method of mapping an element using transmission electron microscopy, the method including:

measuring a roughness and a thickness ($T_1$) of the standard samples using transmission electron microscopy and X-ray reflectivity;

mapping an element of the standard samples using energy dispersive spectroscopy and electron energy loss spectroscopy techniques to obtain a mapping image, and measuring a thickness ($T_2$) using the mapping image; and optimizing mapping conditions of energy dispersive spectroscopy and electron energy loss spectroscopy by finding a condition in which $|T_2-T_1|$ minimized.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The thickness of a nanometer-sized thin film can be precisely measured using X-ray reflectivity (XRR), if the thin film has large surface energy and large density difference such as a film formed of oxides and semiconductors. The thickness can be precisely measured using transmission electron microscopy (TEM) based on a contrast difference without any difficulty if the thin film is crystalline or amorphous and composed of heavy or light atoms. If an energy dispersive spectroscopy (EDS) method of TEM is used to precisely analyze the structure and elements of a nanometer-sized thin film, characteristic X ray energies generated from the nanometer-sized thin film must not overlap to improve resolution. In case an electron energy loss spectroscopy (EELS) method of TEM is used to analyze the structure and elements of a nanometer-sized thin film, if the thin film is formed of a material having a core loss peak with a large S/N ratio, such as an oxide for a nitride, the EELS method has a better resolving power.

The present invention is based on the above-mentioned principle. A standard sample for TEM elemental mapping according to an embodiment of the present invention may have various structures. For example, the standard sample may have a structure in which a crystalline thin film containing heavy atoms is formed on a substrate; an amorphous thin film having a thickness of 1–5 nm, and more preferably 1–3 nm, and being composed of oxides or nitrides containing light atoms is formed on the crystalline thin film; and another crystalline thin film containing heavy atoms is formed on the amorphous thin film. Also, the standard sample may have a structure in which a crystalline thin film containing heavy atoms, an amorphous thin film having a thickness of 6–10 nm, more preferably 8–10 nm, and composed of oxides or nitrides containing light atoms, and another crystalline thin film containing heavy atoms are sequentially stacked. The standard sample may also have a composite structure comprising the above-mentioned two structures.

FIGS. 1A through 1F are sectional views of standard samples, which are multi-layered nanometer-sized thin films, according to embodiments of the present invention.

Figure 1A:
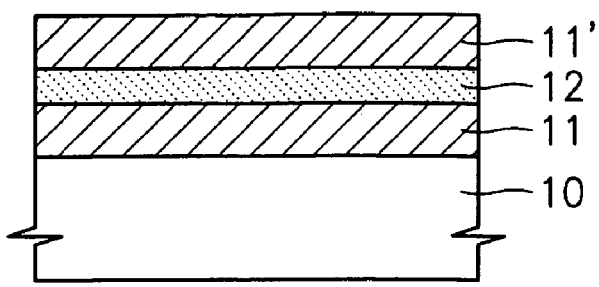
FIGS. 1A through 1F are sectional views of standard samples for elemental mapping according to embodiments of the present invention.

Referring to FIG. 1A, a first crystalline thin film 11 containing heavy atoms is formed on a substrate 10. A first amorphous thin film 12, which includes oxides or nitrides containing light atoms and has the thickness of 1–5 nm, is formed on the first crystalline thin film 11. A second crystalline thin film 11' containing heavy atoms is formed on the first amorphous thin film 12.

Figure 1B:
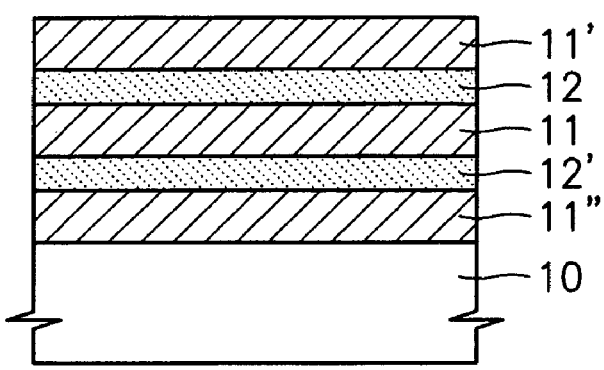
Figure 1C:
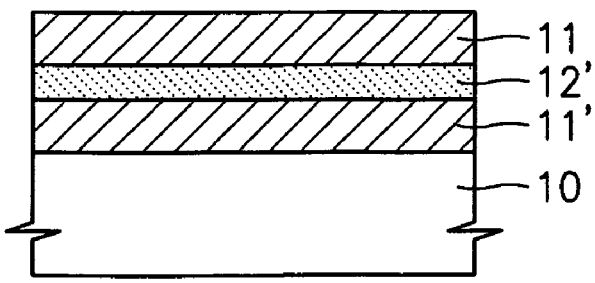
Figure 1D:
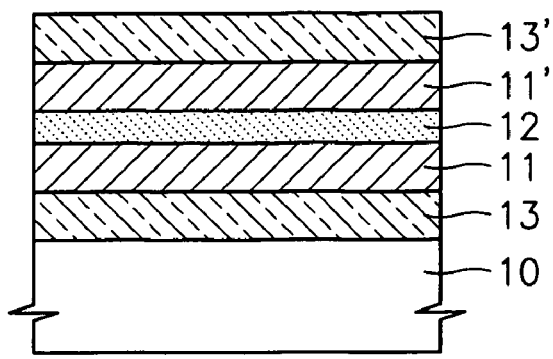

As shown in FIG. 1D, a buffer layer 13 may be further formed between the substrate 10 and the first crystalline thin film 11, and a buffer layer 13' may be further formed on the second crystalline thin film 11'. The buffer layers 13 and 13' facilitate the formation of the first crystalline thin film 11 and the second crystalline thin film 11', and also acts as a seed layer. The buffer layers 13 and 13' include at least an element selected from $SiO_2$, Ta, Ru, Ti, and the like in this exemplary embodiment. Each of the buffer layers 13 and 13' may have a thickness of 1–10 nm.

The standard samples illustrated in FIG. 1A and FIG. 1D can be used for FE-TEM. Accordingly, the thickness of the first amorphous thin film 12 should be in the range of 1–5 nm. If the thickness is outside of this range, the first amorphous thin film 12 is not suitable for a standard sample for current FE-TEMs.

The thicknesses of the first crystalline thin film 11 and the second crystalline thin film 11' may be in the range of 1–50 nm. If the thickness of the first crystalline thin film 11 and the second crystalline thin film 11' are outside of this range, it is difficult to manufacture the first crystalline thin film 11 and the second crystalline thin film 11' using current techniques. Further, the thickness of the standard sample increases, which is undesirable for the manufacturing a TEM specimen. These ranges can vary depending on various conditions and developments in the art.

The substrate 10 may be a silicon substrate, a glass substrate, for example. Any suitable material could be used as the substrate 10.

The standard sample illustrated in FIG. 1B includes a third crystalline thin film 11" containing heavy atoms and a second amorphous thin film 12', which includes oxides or nitrides containing light atoms and has a thickness of 6–10 nm for example, are sequentially deposited between the substrate 10 and the first crystalline thin film 11 of the standard sample illustrated in FIG. 1A. In addition, as shown in FIG. 1E, a buffer layer 13 may further be formed between the substrate 10 and the third crystalline thin film 11", and a buffer layer 13' may be further formed on the second crystalline thin film 11'.

Figure 1E:
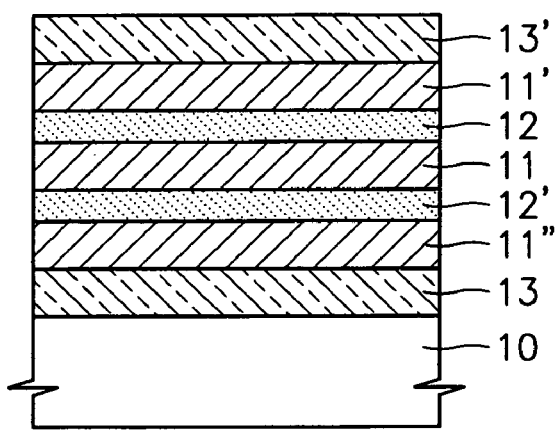

The standard samples illustrated in FIG. 1B and FIG. 1E can be used for both FE-TEM and common TEM, in which a thermal electron gun is used.

In FIG. 1C, a multi-layered nanomater-sized thin film includes a second crystalline thin film 11' containing heavy atoms formed on a substrate 10; a second amorphous thin film 12', which includes oxides or nitrides containing light atoms and has the thickness of 6–10 nm; and a first crystalline thin film 11 formed on a second amorphous thin film 12'.

Figure 1F:
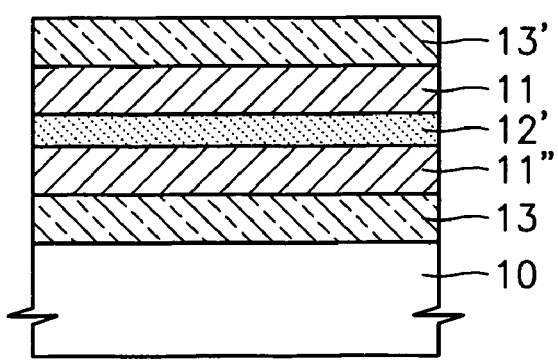

Buffer layers 13 and 13' may be formed between the substrate 10 and the second crystalline thin film 11" or/and on the first crystalline thin film 11, respectively (FIG. 1F).

The standard samples illustrated in FIG. 1C and FIG. 1F can be used for common TEM in which a thermal electron gun is used. In this case, the thickness of the second amorphous thin film 12' may be in the range of 6–10 nm. If the thickness is outside of this range, the standard samples are not suitable for use with current versions of a thermal electron gun.

The heavy atoms included in the first crystalline thin film, the second crystalline thin film, and the third crystalline thin film is an element with an atomic number equal to or greater than 26. The first crystalline thin film, the second crystalline thin film, and the third crystalline thin film containing the heavy atoms may have a single-layered structure, or a multi-layered structure. The thin films are each independently composed of at least an element selected from Ta, NiFe, MnPt, Ru, and CoFe in exemplary embodiments.

The light atoms included in oxides or nitrides of which the first amorphous film or the second amorphous film is an element with an atomic number equal to or less than 25. The first amorphous thin film or the second amorphous thin film, which is composed of oxides or nitrides containing the light atoms, is composed of at least a compound selected from aluminium oxide, manganese oxide, titanium oxide, chromium oxide, silicon oxide, aluminium nitride, silicon nitride, titanium nitride, and the like in exemplary embodiments.

Figure 7:
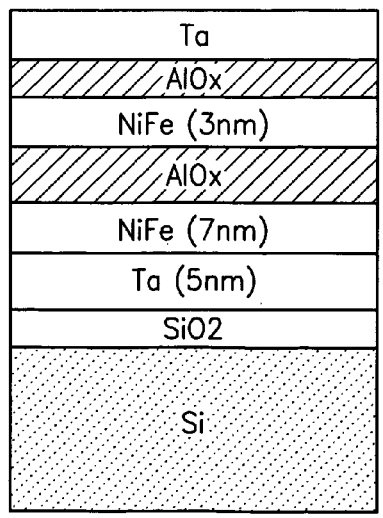
FIG. 7 is a sectional view illustrating a laminated structure of a standard sample according to an embodiment of the present invention.

FIG. 7 is a sectional view illustrating a laminated structure of a standard sample according to an embodiment of the present invention. Referring to FIG. 7, a SiO$_2$ film, a Ta film (thickness: 5 nm), a NiFe film (thickness: 7 nm), a first aluminium oxide film having a thickness of 6–10 nm, a NiFe film (thickness: 3 nm), a second aluminium oxide film having the thickness of 1–5 nm, and a Ta film are sequentially deposited on a silicon substrate. The NiFe film corresponds to the crystalline thin film.

According to another embodiment of the present invention, a multi-layered thin film may include a silicon substrate, a Ta film, a NiFe film, an MnPt film, a CoFe film, a Ru film, a CoFe film, an aluminium oxide film having a thickness of 1–5 nm, a CoFe film, a NiFe film, and a Ta film, which are sequentially stacked. The NiFe film, the MnPt film, the CoFe film, and the Ta film correspond to the amorphous thin film.

Figure 2:
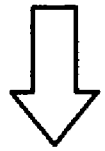
FIG. 2 is a flowchart illustrating an optimized elemental mapping of a multi-layered nanometer-sized thin film in which the standard sample according to an embodiment of the present invention is used.
Figure 2:
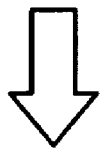

A TEM elemental mapping method using the above-mentioned standard samples will now be described with reference to FIG. 2.

First, a roughness and a thickness ($T_1$) A of a standard film, which is an amorphous thin film composed of oxides or nitrides, in a standard sample is measured using XRR and TEM.

Then, the standard film in the standard sample is mapped using EDS and EELS. Spatial resolution depends on the type of TEM, FE-TEM used for mapping an oxide or nitride thin film having the thickness of 1–5 nm, and conventional TEM is used for mapping an oxide or nitride thin film having a thickness of 6–10 nm. A thickness ($T_2$) of the thin film, which is measured using a mapping image obtained using EDS and EELS, is compared to $T_1$, which is measured using XRR and TEM, to correct the thickness difference caused by TEM type and mapping method. Then, an optimum mapping condition is observed by changing mapping conditions: the optimum condition is when $|T_2-T_1|$ is minimized.

Hereinafter, the present invention will now be described in more detail with reference to the following Examples. These examples are provided for the purpose of illustration and are not intended to limit the scope of the present invention.

EXAMPLE 1

A multi-layered nanometer-sized thin film to be used as a standard sample was prepared by sequentially depositing a Ta film (thickness: 3 nm), a NiFe film (thickness: 3 nm), a MnPt film (thickness: 1.5 nm), a CoFe film (thickness: 2 nm), a Ru film (thickness: 0.8 nm), a CoFe film (thickness: 2.5 nm), an amorphous aluminium oxide film, a CoFe film (thickness: 2.5 nm), a NiFe film (thickness: 4 nm), and a Ta film (thickness: 5 nm) on a silicon substrate.

Figure 3:
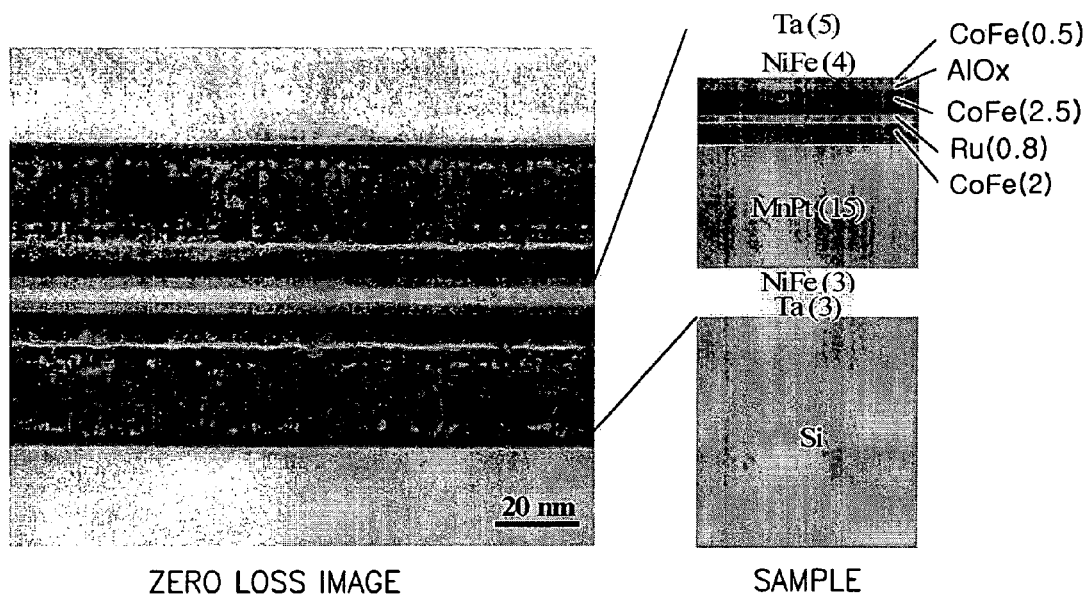
FIG. 3 is a transmission electron microscopy (TEM) image of a multi-layered nanometer-sized thin film according to an embodiment of the present invention.

The standard sample was analysed using TEM, and the results are shown in FIG. 3.

FIG. 3 illustrates a zero loss image of the standard sample produced according to Example 1. Referring to FIG. 3, the measured thickness of the amorphous aluminium oxide film was about 1.2 nm.

Figure 4:
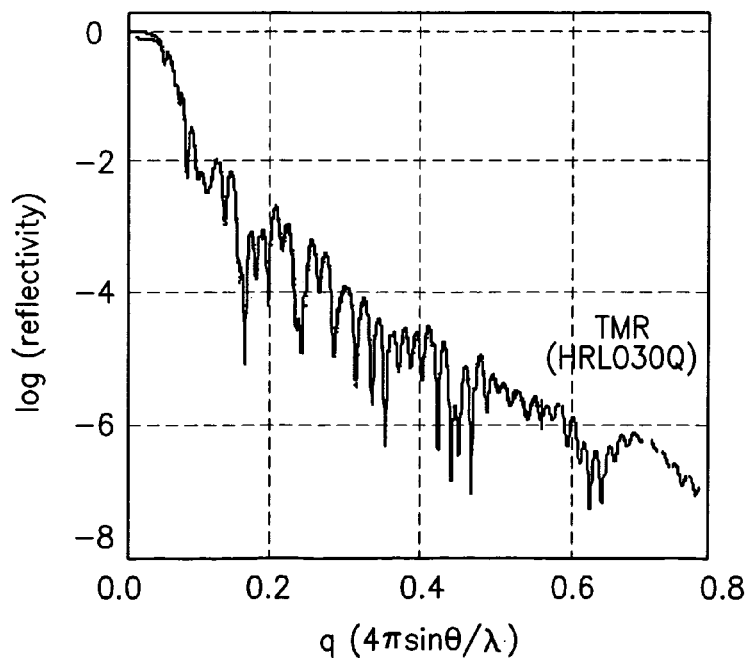
FIG. 4 shows results of 2-wavelength X-ray reflectivity (XRR) performed on the multi-layered nanometer-sized thin film shown in FIG. 3.

The standard sample was analysed using 2-wavelength XRR, and the results are shown in FIG. 4.

Referring to FIG. 4, the measured thickness of the amorphous aluminium oxide film was about 1.0 nm.

Figure 5:
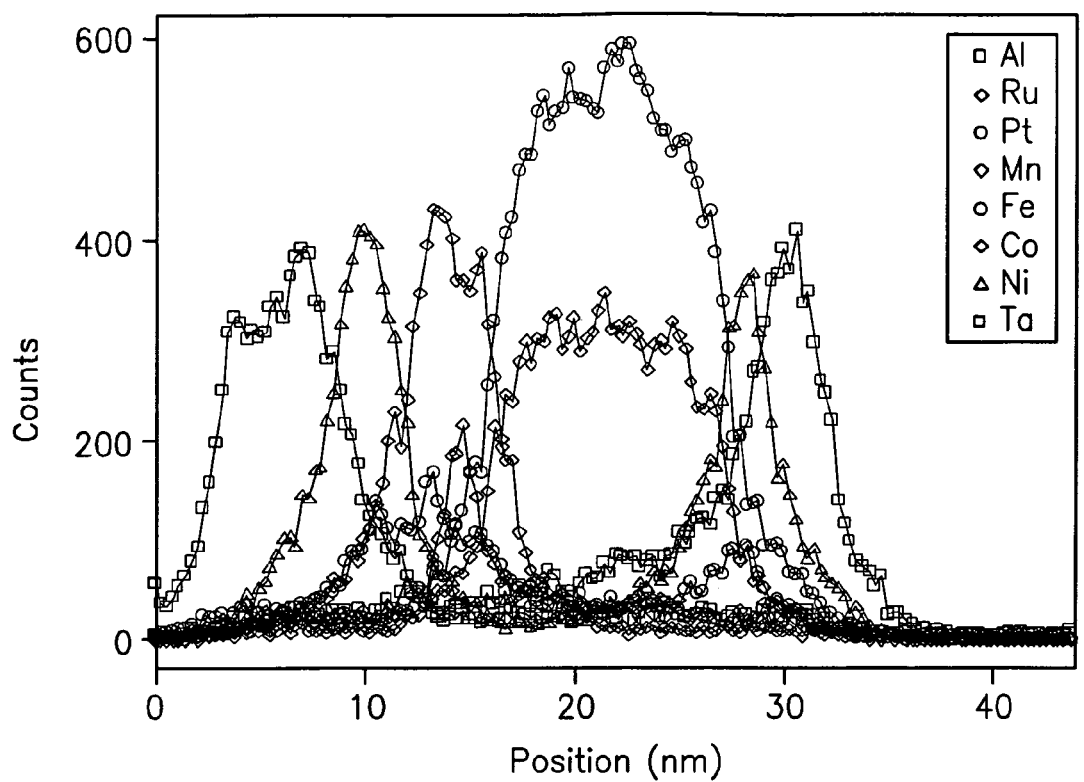
FIG. 5 shows line profile analysis results of energy dispersive spectroscopy (EDS) performed on the multi-layered nanometer-sized thin film shown in FIG. 3.
Figure 5:
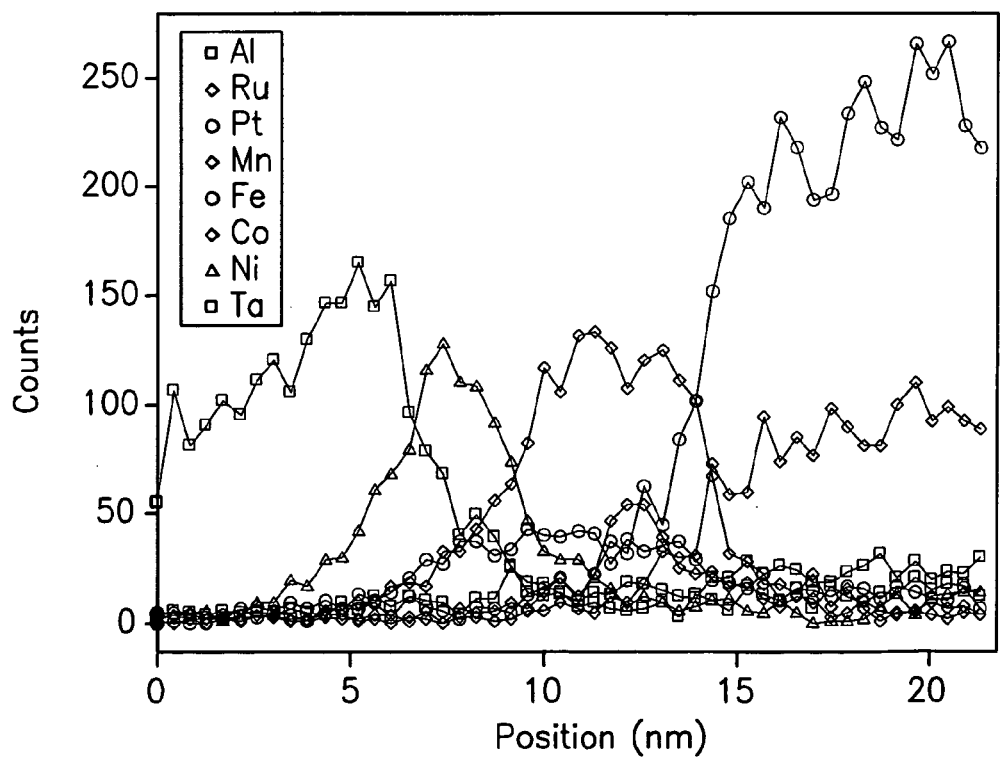

The standard sample was analysed using EDS to obtain line profile analysis data, and the results are shown in FIG. 5.

Referring to FIG. 5, the compositions and the thicknesses of individual layers was identified, and the measured thickness of the amorphous oxide aluminium film was about 4.0 nm.

Figure 6:
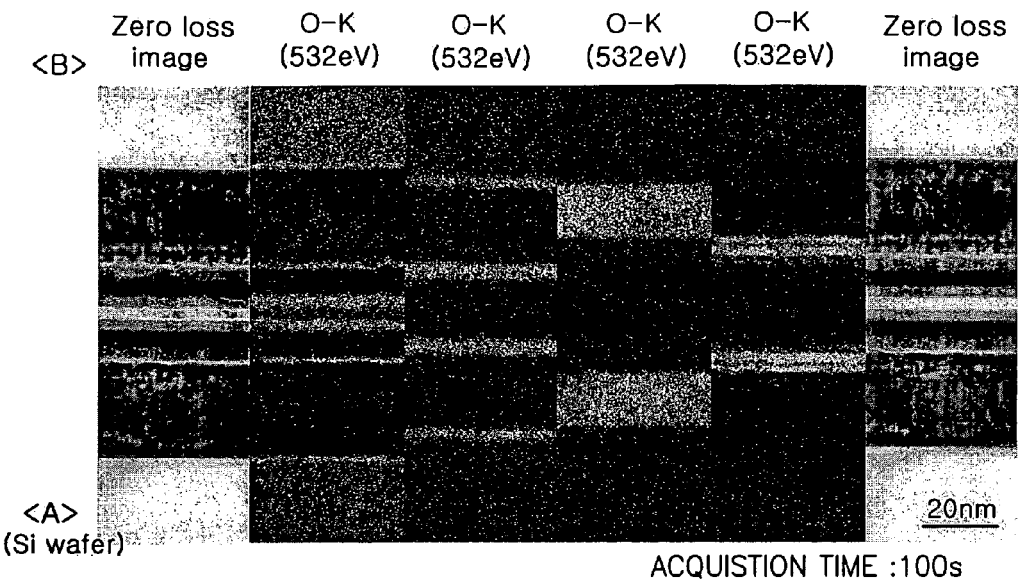
FIG. 6 shows results of time-resolved electron energy loss spectroscopy (EELS) performed on the multi-layered nanometer-sized thin film shown in FIG. 3.

The standard sample was analysed using time-resolved EELS, and the results are shown in FIG. 6.

Referring to FIG. 6, the elemental distribution and thickness are shown 2-dimensionally. It was determined that the measured thickness of the amorphous aluminium oxide film was about 2.8 nm.

In the standard sample according to Example 1, the thickness of an AlO$_x$ film ($1 \leq x \leq 1.5$) was measured using various analysis methods. The results are shown in FIG. 1.

TABLE 1

| Analysis method | Film thickness (nm) |
| --- | --- |
| TEM | 1.2 |
| EDS line profile | 4.0 |
| 1D-EELS | 2.8 |
| XRR | 1.0 |

Referring to Table 1, the thicknesses of the AlO$_x$ film measured by TEM and XRR are 1.2 nm and 1.0 nm, respectively. The thicknesses of the AlO$_x$ film measured by EDS and EELS are 4.0 nm and 2.8 nm, respectively. EDS and EELS mapping conditions were optimised so that the thicknesses of the AlO$_x$ film measured by EDS and EELS are nearly equal to the thicknesses of the AlO$_x$ film measured by TEM and XRR. Under the optimum conditions, elemental mapping was carried out.

A stand sample for TEM elemental mapping according to an embodiment of the present invention includes an amorphous thin film having a thickness of 1–10 nm and is composed of oxides or nitrides. The standard sample can be used not only to correct SEM, EDS, and EELS mapping results of a multi-layered nanometer-sized thin film, but also to optimise mapping conditions.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A standard sample for transmission electron microscope elemental mapping, the standard sample comprising:
    a substrate;
    a first crystalline thin film containing heavy atoms formed on the substrate;
    a first amorphous thin film comprising oxides or nitrides containing light atoms and having a thickness of 1–5 nm formed on the first crystalline thin film; and
    a second crystalline thin film containing heavy atoms formed on the first amorphous thin film.

2. The standard sample of claim 1, further comprising a buffer layer deposited on the second crystalline thin film.

3. The standard sample of claim 2, wherein the buffer layer comprises at least one material selected from the group consisting of SiO$_2$, Ta, Ru, and Ti.

4. The standard sample of claim 1, further comprising a buffer layer interposed between the substrate and the first crystalline thin film.

5. The standard sample of claim 4, wherein the buffer layer comprises at least one material selected from the group consisting of SiO$_2$, Ta, Ru, and Ti.

6. The standard sample of claim 1, further comprising a buffer layer, a third crystalline thin film containing heavy atoms, and a second amorphous thin film comprising oxides or nitrides containing light atoms and having a thickness of 6–12 nm interposed between the substrate and the first crystalline thin film.

7. The standard sample of claim 6, wherein a buffer layer is further formed on the second crystalline layer.

8. The standard sample of claim 1, wherein the heavy atoms contained in the first crystalline thin film and the second crystalline thin film are elements with atomic numbers equal to or greater than 26.

9. The standard sample of claim 1, wherein each of the first crystalline thin film and the second crystalline thin film have a single-layered structure or a multi-layered structure, and independently comprises at least an element selected from the group consisting of Ta, NiFe, MnPt, Ru, and CoFe.

10. The standard sample of claim 1, wherein the first amorphous thin film include elements with atomic numbers equal to or less than 25.

11. The standard sample of claim 1, wherein the first amorphous thin film comprises at least a compound selected from the group consisting of aluminum oxide, manganese oxide, titanium oxide, chromium oxide, silicon oxide, aluminum nitride, silicon nitride, and titanium nitride.

12. The standard sample of claim 1, comprising a silicon substrate, a SiO$_2$ film, a Ta film, a NiFe film, a first aluminum oxide having a thickness of 6–10 nm, a NiFe film, a second aluminum oxide having a thickness of 1–5 nm, and a Ta film stacked sequentially.

13. The standard sample of claim 1, comprising a silicon substrate, a Ta film, a NiFe film, an MnPt film, a CoFe film, a Ru film, a CoFe film, an aluminium oxide film having a thickness of 1–5 nm, a CoFe film, a NiFe film, and a Ta film stacked sequentially.

14. A method of mapping an element using transmission electron microscopy, the method comprising:
    measuring a roughness and a thickness ($T_1$) of a standard sample of claim 1 using transmission electron microscopy and X-ray reflectivity;
    mapping an element of the standard sample of claim 1 using energy dispersive spectroscopy (EDS) and electron energy loss spectroscopy (EELS) techniques to obtain a mapping image, and measuring a thickness ($T_2$) using the image; and
    optimizing mapping conditions of energy dispersive spectroscopy and electron energy loss spectroscopy by finding a condition in which $|T_2-T_1|$ minimized.

15. The method of claim 14, wherein the standard sample comprises a silicon substrate, a SiO$_2$ film, a Ta film, a NiFe film, a first aluminum oxide having a thickness of 6–10 nm, a NiFe film, a second aluminum oxide having a thickness of 1–5 nm, and a Ta film stacked sequentially.

16. The method of claim 14, wherein the standard sample comprises a silicon substrate, a Ta film, a NiFe film, an MnPt film, a CoFe film, a Ru film, a CoFe film, an aluminium oxide film having a thickness of 1–5 nm, a CoFe film, a NiFe film, and a Ta film stacked sequentially.

17. A standard sample for transmission electron microscope elemental mapping, the standard sample comprising:
    a substrate;
    a first crystalline thin film containing heavy atoms formed on the substrate;
    a first amorphous thin film comprising oxides or nitrides containing light atoms and having a thickness of 6–10 nm formed on the first crystalline thin film; and
    a second crystalline thin film containing heavy atoms formed on the second amorphous thin film.

18. The standard sample of claim 17, further comprising a buffer layer deposited on the second crystalline thin film.

19. The standard sample of claim 18, wherein the buffer layer comprises at least an element selected from the group consisting of SiO$_2$, Ta, Ru, and Ti.

20. The standard sample of claim 17, further comprising a buffer layer deposited between the substrate and the first crystalline thin film.

21. The standard sample of claim 20, wherein the buffer layer comprises at least an element selected from the group consisting of SiO$_2$, Ta, Ru, and Ti.

22. The standard sample of claim 17, wherein each of the first crystalline thin film and the second crystalline thin film comprises elements with atomic numbers equal to or greater than 26.

23. The standard sample of claim 17, wherein each of the first crystalline thin film and the second crystalline thin film has a single-layered structure or a multi-layered structure, and independently comprises at least a compound selected from the group consisting of Ta, NiFe, MnPt, Ru, and CoFe.

24. The standard sample of claim 17, the light atoms contained in the first amorphous film includes elements with atomic numbers equal to or less than 25.

25. The standard sample of claim 17, wherein the second amorphous film comprises at least a compound selected from the group consisting of aluminum oxide, manganese oxide, titanium oxide, chromium oxide, silicon oxide, aluminum nitride, silicon nitride, and titanium nitride.

26. A method of mapping an element using transmission electron microscopy, the method comprising:
   measuring a roughness and a thickness ($T_1$) of a standard sample of claim 17 using transmission electron microscopy and X-ray reflectivity;
   mapping an element of the standard sample of claim 17 using energy dispersive spectroscopy (EDS) and electron energy loss spectroscopy (EELS) techniques to obtain a mapping image, and measuring a thickness ($T_2$) using the image; and
   optimizing mapping conditions of energy dispersive spectroscopy and electron energy loss spectroscopy by finding a condition in which $|T_2-T_1|$ minimized.

* * * * *